United States Patent
Yabutani et al.

(10) Patent No.: US 11,517,636 B2
(45) Date of Patent: Dec. 6, 2022

(54) ANALYZER

(71) Applicants: Hitachi High-Tech Corporation, Tokyo (JP); Roche Diagnostics Operations, Inc., Indianapolis, IN (US)

(72) Inventors: Hisashi Yabutani, Tokyo (JP); Takeshi Ishida, Tokyo (JP); Yoshihiro Yamashita, Tokyo (JP); Taku Sakazume, Tokyo (JP); Michaela Windfuhr, Penzberg (DE); Bernhard Hauptmann, Penzberg (DE); Andreas Finke, Penzberg (DE)

(73) Assignees: Hitachi High-Tech Corporation, Tokyo (JP); Roche Diagnostics Operations, Inc., Indiana, IN (US)

( * ) Notice: Subject to any disclaimer, the term of this patent is extended or adjusted under 35 U.S.C. 154(b) by 379 days.

(21) Appl. No.: 16/640,971

(22) PCT Filed: Sep. 10, 2018

(86) PCT No.: PCT/JP2018/033364
§ 371 (c)(1),
(2) Date: Feb. 21, 2020

(87) PCT Pub. No.: WO2019/082524
PCT Pub. Date: May 2, 2019

(65) Prior Publication Data
US 2020/0171182 A1    Jun. 4, 2020

(30) Foreign Application Priority Data

Oct. 25, 2017   (JP) .............................. JP2017-206198

(51) Int. Cl.
*A61L 2/10*    (2006.01)
*C02F 1/32*    (2006.01)
*G01N 35/10*   (2006.01)

(52) U.S. Cl.
CPC .................... *A61L 2/10* (2013.01); *C02F 1/32* (2013.01); *C02F 2201/326* (2013.01); *G01N 35/1002* (2013.01)

(58) Field of Classification Search
CPC ........ A61L 2/10; C02F 1/32; C02F 2201/326; C02F 1/325; G01N 35/1002;
(Continued)

(56) References Cited

U.S. PATENT DOCUMENTS 5,459,322 A * 10/1995 Warkentin .......... A61M 1/3681
                                          250/455.11
2010/0193709 A1 * 8/2010 Dalton .................. A61L 2/10
                                          250/504 R
(Continued)

FOREIGN PATENT DOCUMENTS

JP      63-163168 A    7/1988
JP      2-42641 U      3/1990
(Continued)

OTHER PUBLICATIONS

International Search Report (PCT/ISA/210) issued in PCT Application No. PCT/JP2018/03364 dated Nov. 13, 2018 with English translation (four (4) pages).
(Continued)

*Primary Examiner* — Jason L McCormack
(74) *Attorney, Agent, or Firm* — Crowell & Moring LLP

(57) ABSTRACT

An analyzer that has a simple configuration, that is inexpensive, that can improve safety, and that can inhibit proliferation of microorganisms using ultraviolet light is realized. A first electric power switch, a second electric power switch, and a third electric power switch are connected in series between an ultraviolet LED that irradiates an interior of a shared reagent storage container with ultraviolet light and a power supply that supplies electric power to the
(Continued)

ultraviolet LED. The first electric power switch, the second electric power switch, and the third electric power switch are configured with two contact points and a connection section that connects and disconnects the two contact points. The first electric power switch is opened when a reagent storage door is opened, and the second electric power switch is opened in response to an action of extracting an ultraviolet irradiation section from a shared reagent storage container. The third electric power switch is opened when an amount of the reagent within the shared reagent storage container is equal to or smaller than a constant value. When one of the first electric power switch, the second electric power switch, and the third electric power switch is opened, supply of the electric power to the ultraviolet LED is intercepted.

7 Claims, 8 Drawing Sheets

(58) Field of Classification Search
CPC ... G01N 35/00594; G01N 2035/00277; G01N 2035/00673
USPC ........................................ 422/64; 250/455.11
See application file for complete search history.

(56) References Cited

U.S. PATENT DOCUMENTS

2017/0336427 A1* 11/2017 Long .................. G01N 35/1081
2019/0310275 A1 10/2019 Ishida et al.

FOREIGN PATENT DOCUMENTS

| JP | 6-12773 U | 2/1994 |
| JP | 9-99921 A | 4/1997 |
| JP | 2001-247108 A | 9/2001 |
| JP | 2008-224122 A | 9/2008 |
| JP | 2017-87153 A | 5/2017 |
| WO | WO 2017/212808 A1 | 12/2017 |

OTHER PUBLICATIONS

Japanese-language Written Opinion (PCT/ISA/237) issued in PCT Application No. PCT/JP2018/03364 dated Nov. 13, 2018 (seven (7) pages).

International Preliminary Report on Patentability (PCT/IB/338 & PCT/IB/373) issued in PCT Application No. PCT/JP2018/033364 dated May 7, 2020, including English translation (Japanese-language Written Opinion (PCT/ISA/237) previously filed on Feb. 21, 2020) (12 pages).

* cited by examiner

ANALYZER

BACKGROUND OF THE INVENTION

1. Field of the Invention

The present invention relates to an analyzer that analyzes a specimen by using a reagent.

2. Description of the Related Art

There is known a type of analyzer, among analyzers, that adds a reagent to a sample to be analyzed for deriving an analysis result. The reagent mentioned herein is not limited to a reaction reagent that produces a reaction with the sample but a diluent, a detergent, a buffer solution, and a surface-active agent that activates an interface between an object to be analyzed and the reaction reagent are also reagents in a broad sense.

It is, therefore, necessary to hold reagent containers that store these reagents in an interior of or near an exterior of the analyzer.

The analysis result depends on components contained in the reagent to be added; thus, alteration of the components of the reagent to be added over time reduces the reproducibility of the analysis result. Examples of causes for a change over time include decomposition or alteration of the components of the reagent with a change in a reagent temperature, a change in an ambient humidity, and activity of microorganisms entering an interior of a reagent storage container.

Owing to this, measures are taken for avoiding the change of the reagent within the reagent container over time or delaying the change of the reagent over time. Specifically, there is known a method of alleviating the change of the reagent over time by managing the reagent in preset temperature and humidity ranges or by intercepting the entry of microorganisms into the reagent. A feature mounted for making the proliferation of the entering microorganisms impossible or inhibiting the metabolism of the microorganisms in case of the entry of microorganisms into the reagent is often more cost effective than a feature mounted for completely preventing the entry of the microorganisms into the reagent.

JP-2001-247108-A does not relate to an analyzer but particularly discloses a container sterilization method that does not need many processes and does not need a wastewater treatment as means for sterilizing an object stored in a container.

Furthermore, JP-1997-099921-A does not relate to an analyzer like JP-2001-247108-A but discloses a food container sterilization method for sterilizing a food container without the need of heat sterilization and without the loss of flavor of a food in the container.

SUMMARY OF THE INVENTION

The technique described in JP-2001-247108-A is configured with a controller that controls an ultraviolet flash lamp in such a manner as to irradiate an inner side surface of a container to be sterilized with an optical pulse after a sensor detects the insertion of the ultraviolet flash lamp into the container.

However, with the technique described in JP-2001-247108-A, there is a concern that the optical pulse is emitted from the ultraviolet flash lamp even in a state in which the ultraviolet flash lamp is not inserted into the container to be sterilized during a failure of the sensor or the controller.

Furthermore, the technique described in JP-1997-099921-A uses an optical fiber for guiding an ultraviolet laser beam. In addition, the technique uses elevating means for inserting or extracting the optical fiber into or from the container to be sterilized. This elevating means is provided with a position sensor that detects an elevation position and turns on or off oscillation of the ultraviolet laser beam in response to a vertical position of a tip end portion of the optical fiber attached to the elevating means using control means.

With the technique described in JP-1997-099921-A, there is a concern that the ultraviolet laser beam is emitted even when the tip end portion of the optical fiber is located outside of the container to be sterilized during a failure of the control means or the elevating means.

Although it is conceivable that a cold insulation device that provides entire cold insulation is installed in an analyzer in a case of performing a treatment for inhibiting the proliferation of microorganisms in the reagent, the installation undesirably increases a cost of the analyzer.

Thus, it is preferable to apply a treatment for inhibiting the proliferation of microorganisms using ultraviolet light to the analyzer like JP-2001-247108-A and JP-1997-099921-A; however, when the use of ultraviolet light is applied to the analyzer, it is desirable to prevent an operator or the like from being irradiated with the ultraviolet light and achieve further improvement of safety.

However, applying the techniques described in JP-2001-247108-A and JP-1997-099921-A to the analyzer involves a large increase in the cost of the analyzer since the controller exercises light emission control to make a configuration complicated in the techniques described in JP-2001-247108-A and JP-1997-099921-A. As a result, it has been difficult to improve safety measures without involving the large cost increase.

An object of the present invention is to provide an analyzer that can improve safety by performing a microorganism inactivation treatment using ultraviolet light and using a simple, inexpensive configuration.

To attain the object, the present invention is configured as follows.

An analyzer includes: an analysis section that analyzes a specimen within a reaction container that accommodates a reagent and the specimen; a liquid storage container that stores a liquid for use in analysis; an ultraviolet irradiation section that irradiates the liquid in the liquid storage container with ultraviolet light; a power supply that supplies electric power to the ultraviolet irradiation section; a liquid storage container storage room that stores the liquid storage container and the ultraviolet irradiation section; and a first electric current switch that closes connection between the power supply and the ultraviolet irradiation section when a storage door of the liquid storage container storage room is closed, and that opens the connection between the power supply and the ultraviolet irradiation section and stops supply of the electric current to the ultraviolet irradiation section when the storage door is opened.

ADVANTAGE OF THE INVENTION

According to the present invention, it is possible to improve safety by performing a microorganism inactivation treatment using ultraviolet light and using a simple, inexpensive configuration.

DESCRIPTION OF THE PREFERRED EMBODIMENTS

Embodiments will be described hereinafter with reference to the drawings.

EMBODIMENTS

First Embodiment

An outline of an analyzer to which a first embodiment is applied will first be described.

Analysis mentioned herein refers to clinical chemical analysis. That is, in the analysis, gathered blood is separated into a serum and a blood clot by centrifugation and the obtained serum is mixed with various reagents. Furthermore, in the analysis, electrical signal conversion values of a chemical reaction produced as a result of mixture are acquired as time series variations and component concentrations of the serum are determined. A system that automates part of or all of these series of work is referred to as either "automatic analyzer" or simply "analyzer."

Figure 1:
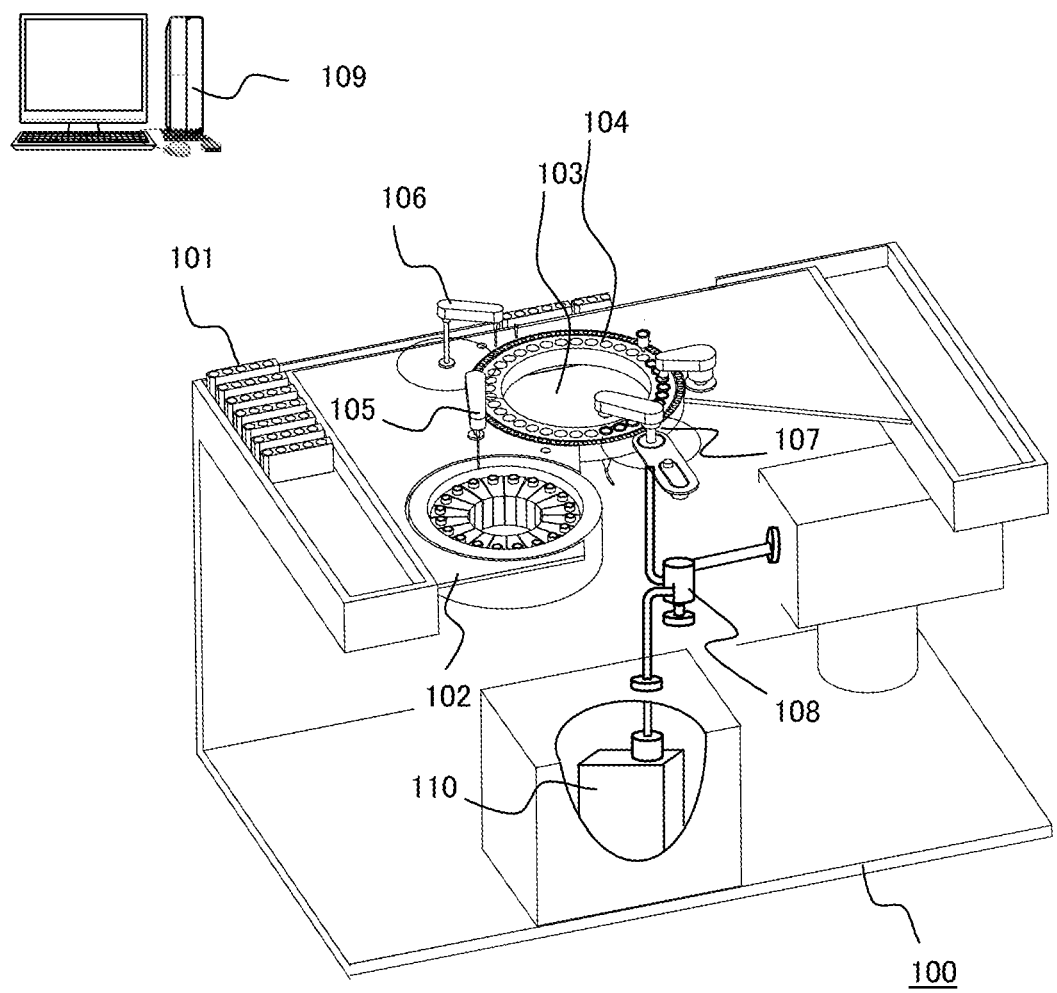
FIG. 1 is a perspective view showing a schematic configuration of an analyzer.

FIG. 1 is a perspective view showing a schematic configuration of an analyzer 100.

In FIG. 1, the analyzer 100 includes a specimen transport mechanism 101, a reaction reagent storage section 102, a reaction tank 103 where reaction containers 104 are disposed, a reaction reagent dispensing mechanism 105, a specimen dispensing mechanism 106, a shared reagent dispensing mechanism 107, a shared reagent storage container 110, a syringe 108, and a control section 109.

The specimen transport mechanism 101 transports a specimen to be analyzed to an operating range of the specimen dispensing mechanism 106. The reaction reagent storage section 102 stores various reaction reagents necessary for analysis. The reaction tank 103 includes a plurality of reaction containers 104 each producing a reaction between the specimen and the reaction reagent.

The reaction reagent dispensing mechanism 105 performs suction of any of the reagents stored in the reaction reagent storage section 102 and delivery thereof to the reaction tank 103. The specimen dispensing mechanism 106 performs suction of the specimen transported by the specimen transport mechanism 101 and delivery thereof to each reaction container 104 provided in the reaction tank 103.

The shared reagent dispensing mechanism 107 performs suction of a shared reagent stored in the shared reagent storage container 110 and delivery thereof to each reaction container 104.

The control section 109 controls each constituent component of the analyzer to operate. In addition, the control section 109 has a function to analyze the specimen and store an analysis result, and a function to indicate the analysis result. The control section 109 can be defined as an analysis section.

In the analyzer 100 configured as described above, an ultraviolet irradiation section according to the first embodiment inhibits the proliferation of microorganisms in the reagent stored in the shared reagent storage container 110.

While FIG. 1 shows that the shared reagent storage container 110 is disposed in a housing interior of the analyzer 100, the shared reagent storage container 110 may be disposed in a housing exterior. The shared reagent storage container 110 needs to be able to continuously supply a specified amount of the reagent for analysis operation by the analyzer 100.

The first embodiment of inactivating bacteria within the shared reagent storage container 110 shown in FIG. 1 will be described with reference to FIG. 2. The shared reagent will be simply referred to as "reagent," hereinafter.

Figure 2:
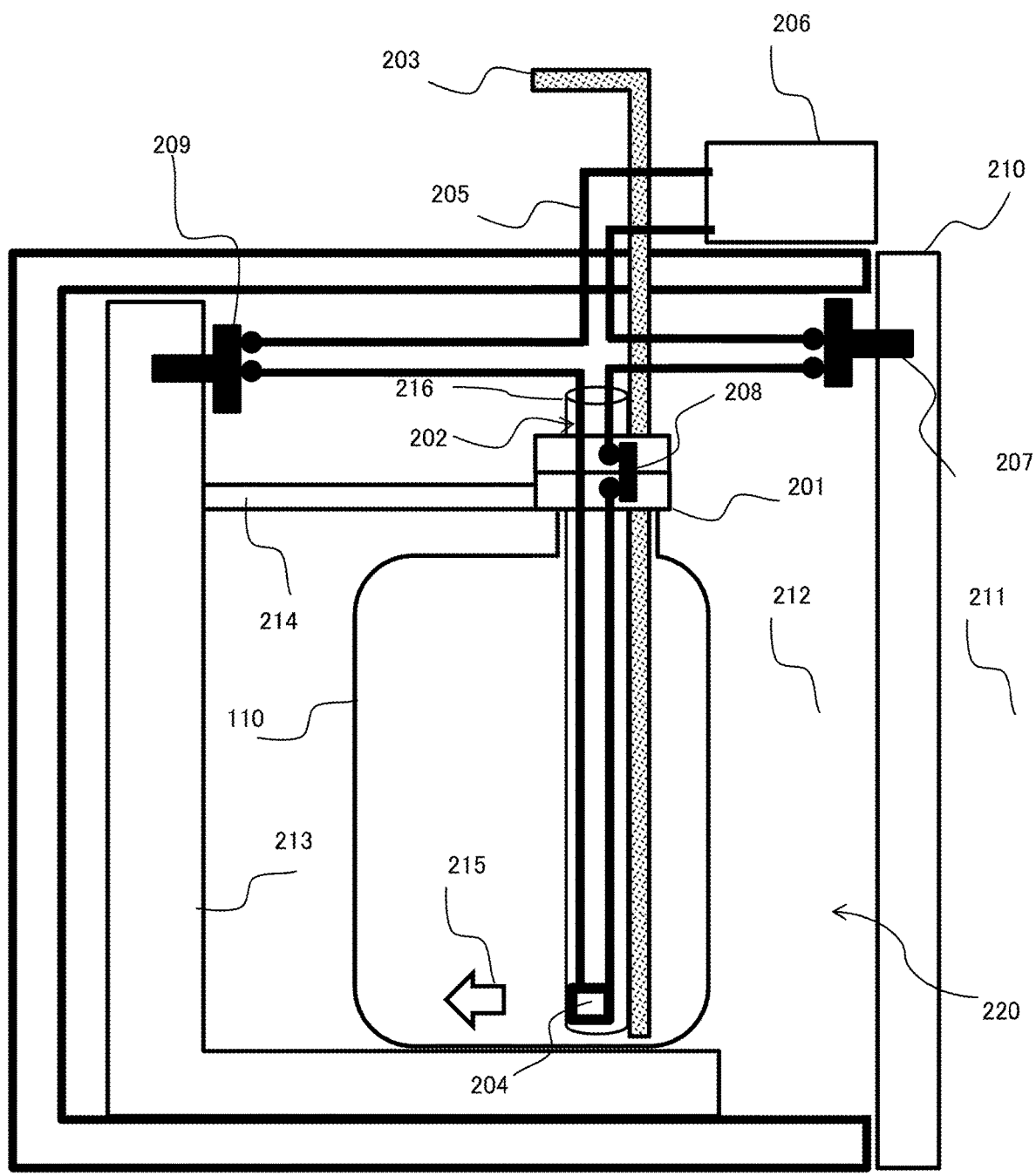
FIG. 2 is a schematic configuration diagram of an ultraviolet irradiation section according to a first embodiment.

FIG. 2 is a schematic configuration diagram of the ultraviolet irradiation section according to the first embodiment.

In FIG. 2, the shared reagent storage container 110 has a reagent storage container opening portion 201, and an ultraviolet irradiation section 202 and a reagent suction nozzle 203 are inserted into the shared reagent storage container 110 from this opening portion 201. The reagent absorbed from the reagent suction nozzle 203 by suction is fed to the shared reagent dispensing mechanism 107 (FIG. 1) for use in an analytical reaction.

The ultraviolet irradiation section 202 includes an ultraviolet LED 204 that emits light at a wavelength in an ultraviolet range to a neighborhood of a bottom surface of the shared reagent storage container 110, and the ultraviolet LED 204 is connected to a power supply 206 by a normal interconnection line 205. Furthermore, the ultraviolet irradiation section 202 is stored in a storage cylinder 216 for preventing the ultraviolet LED 204 and the normal interconnection line 205 from contacting the reagent. A material, such as quartz glass, that transmits ultraviolet light and that is not decomposed by the ultraviolet light is appropriate as a material of the storage cylinder 216.

On the other hand, a resin higher in strength than the quartz glass may be used if the resin can prevent the ultraviolet LED 204 and the normal interconnection line 205 from contacting the reagent, transmits the ultraviolet light, and is not decomposed by the ultraviolet light. Using the resin higher in strength than the quartz glass as the material of the storage cylinder 216 can reduce a concern of damaging the ultraviolet irradiation section 202 when a user of the analyzer 100 operates the shared reagent storage container 110.

The ultraviolet LED 204 emits ultraviolet light at a wavelength of 200 to 300 nm. The ultraviolet light at this wavelength damages genes (DNAs or RNAs) of bacteria of interest. The ultraviolet light in this wavelength range stops metabolism of the genes of the bacteria. As a result, the ultraviolet light inhibits the proliferation of microorganisms. It is desirable that the ultraviolet LED 204 is configured to selectively emit ultraviolet light at a wavelength that is effective for inhibition of the proliferation of microorganisms and that does not alter components of the reagent.

Specifically, the ultraviolet LED 204 can appropriately select the wavelength by selecting a type of the ultraviolet LED 204 itself and thereby selecting an irradiation wavelength or by using a filter (not shown in FIG. 2) that transmits or interrupts ultraviolet light at specific wavelengths for the ultraviolet LED 204.

It is noted that the ultraviolet LED 204 is disposed such that an ultraviolet generation direction thereof is oriented to an opposite direction 215 to a direction toward a reagent storage door 210. This is intended to avoid exposure of the user of the analyzer 100, who opens the reagent storage door 210 and approaches the shared reagent storage container 110, to ultraviolet light by limiting an ultraviolet irradiation direction to the opposite direction to the direction in which this user approaches the shared reagent storage container 110.

The power supply 206 supplies a current necessary for the ultraviolet LED 204 to emit ultraviolet light to the ultraviolet LED 204 via the normal interconnection line 205. The normal interconnection line 205 includes lines connecting electric power switches 207, 208, and 209 and the power supply 206 to one another.

The first electric power switch 207 operates as the reagent storage door 210 is opened and closed, and supplies and intercepts electric power. That is, the first electric power switch 207 supplies the electric power to the ultraviolet LED 204 when the reagent storage door 210 is in a closed state, and intercepts the electric power when the reagent storage door 210 is in an open state. It is noted that the reagent storage door 210 is intended to prevent penetration of mine dust into the analyzer 100 and to avoid contact of the user with an operating section within the analyzer 100.

In addition to purposes of preventing the penetration of the mine dust and avoiding the contact, the reagent storage door 210 also function to shield the user of the analyzer 100 from exposure to the ultraviolet light emitted by the ultraviolet LED 204. The reagent storage door 210 may be used as temperature insulation means when it is necessary to keep constant a temperature of an analyzer housing interior 212 with respect to a temperature of an analyzer housing exterior 211.

The reagent storage container 110, the ultraviolet irradiation section 202, a holding stand 213, the first electric power switch 207, the second electric power switch 208, and the third electric power switch 209 are disposed within a reagent storage room 220. The reagent storage room 220 is configured to be opened and closed by the reagent storage door 210.

The first electric power switch 207 will be described with reference to FIG. 3. It is noted that FIG. 3 shows the simplified second switch 208.

Figure 3:
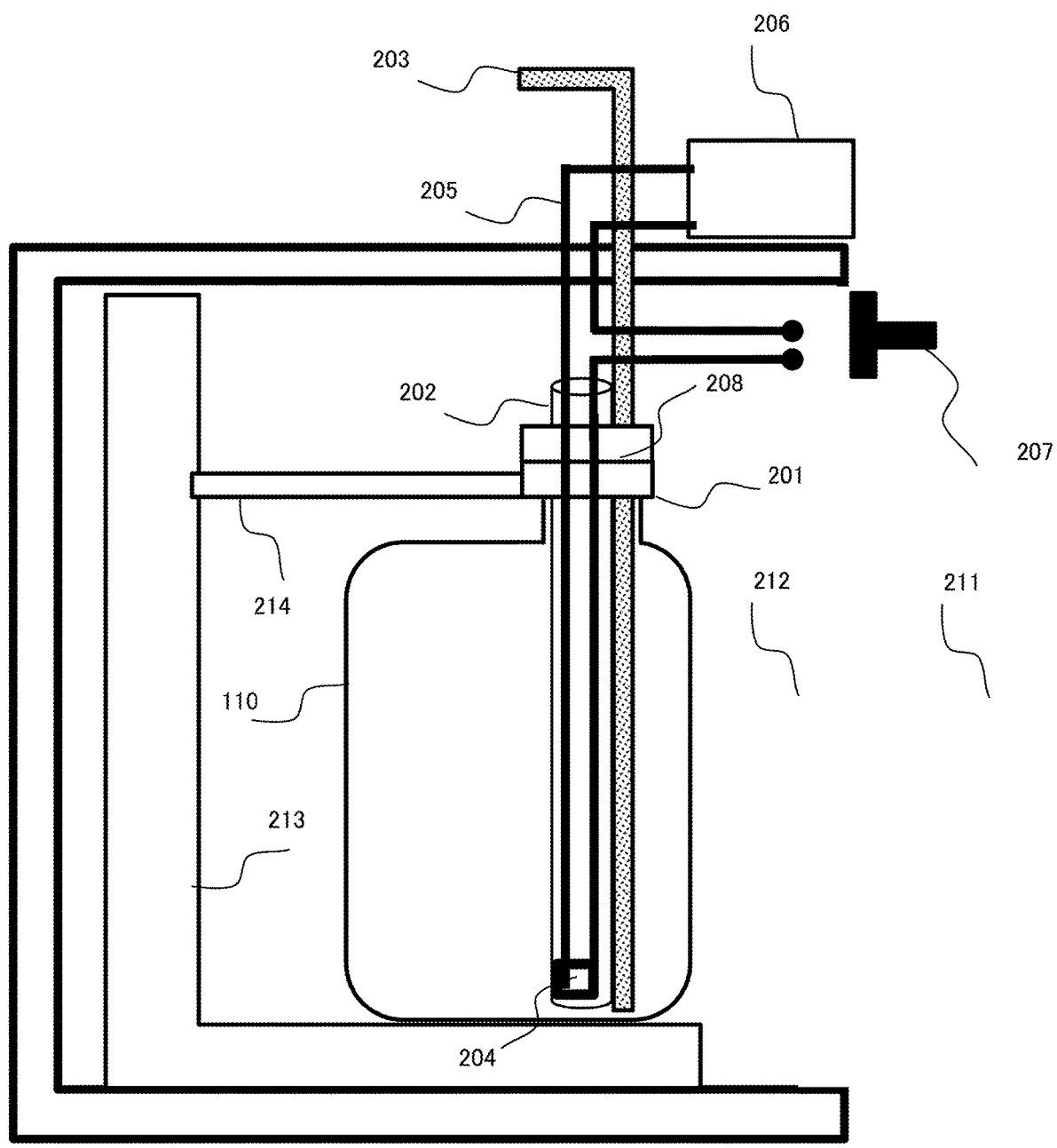
FIG. 3 shows that a reagent storage door, which splits off an analyzer interior from an analyzer exterior, is in an open state.

FIG. 3 shows that the reagent storage door 210, which splits off the analyzer housing interior 212 from the analyzer housing exterior 211, is in the open state. In FIG. 3, the first electric power switch 207 is mounted such that the first electric power switch 207 turns into a closed state and supplies the electric power to the ultraviolet irradiation section 202 when the reagent storage door 210 is in the closed state, and turns into an open state, intercepts the electric power, and prevents the ultraviolet irradiation section 202 from emitting ultraviolet light when the reagent storage door 210 is in the open state. Therefore, when the reagent storage door 210 is in the open state, the switch 207 does not supply the electric power.

Configuring the first electric power switch 207 in this way enables supply of the electric power to be stopped immediately when the user of the analyzer 100 opens the reagent storage door 210 for replacement or the like of the shared reagent storage container 110 even during the supply of the electric power to the ultraviolet LED 204 and irradiation with the ultraviolet light from the ultraviolet LED 204 to inactivate bacteria within the shared reagent storage container 110. The ultraviolet LED 204 thereby stops emitting ultraviolet light and it is possible to avoid exposure of the user to the ultraviolet light.

The second electric power switch 208 supplies and intercepts the electric power as the ultraviolet irradiation section 202 is inserted into and extracted from the shared reagent storage container 110. That is, the second electric power switch 208 supplies the electric power to the ultraviolet LED 294 when the ultraviolet irradiation section 202 is in a state of being inserted into the shared reagent storage container 110, and intercepts the electric power when the ultraviolet irradiation section 202 is in a state of being extracted from the shared reagent storage container 110. The ultraviolet irradiation section 202 is fixed to the reagent suction nozzle 203, and the second electric power switch 208 turns into an open state when the reagent suction nozzle 203 is extracted from the shared reagent storage container 110.

A purpose of using the second electric power switch 208 is to prevent portions other than an interior of the shared reagent storage container 110 from being irradiated with the ultraviolet light. It is known that transmittance of the ultraviolet light is low. The transmittance of the ultraviolet light at a wavelength of 300 nm or shorter transmitted by even polyethylene terephthalate (PET) normally used for a storage container is less than 5% (Fabrication of concave gratings by curved surface UV-nanoimprint lithography, Yung-Pin Chen, et al., 2008 American Vacuum Society).

In a state in which the ultraviolet irradiation section 202 is inserted into the shared reagent storage container 110, it is possible to reduce irradiation of surrounding constituent components other than the shared reagent storage container 110 with the ultraviolet light. Using this second switch 208 can dispense with the sensor that is disclosed in JP-2001-247108-A and that detects the insertion of the ultraviolet flash lamp into the container to be irradiated with the ultraviolet light.

The second electric power switch 208 will next be described with reference to FIG. 4.

Figure 4:
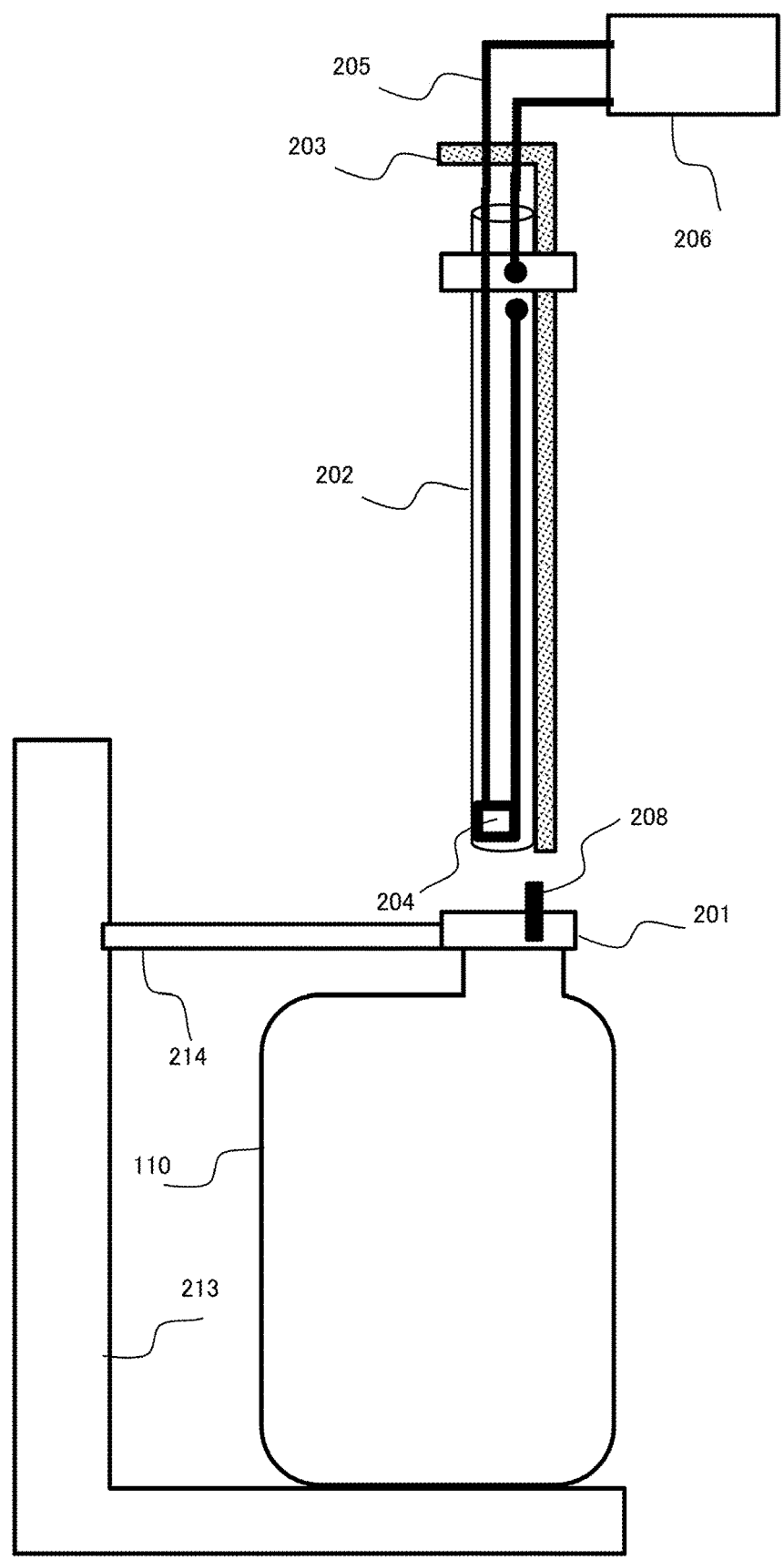
FIG. 4 shows a state in which the ultraviolet irradiation section and a reagent suction nozzle are extracted from a shared reagent storage container installed on a holding stand.

FIG. 4 shows a state in which the ultraviolet irradiation section 202 and the reagent suction nozzle 203 are extracted from the shared reagent storage container 110 installed on the holding stand 213.

In FIG. 4, the second electric power switch 208 is fixed to the opening portion 201 of the shared reagent storage container 110. Furthermore, the opening portion 201 is fixed to the holding stand 213 using an opening portion fixture 214. Fixing the second electric power switch 208 and the opening portion 201 in this way enables the second electric power switch 208 to change from the closed state to the open state when the ultraviolet irradiation section 202 and the reagent suction nozzle 203 are extracted from the shared reagent storage container 110. Turning the second electric power switch 208 into the open state makes it possible to realize a structure of preventing irradiation with the ultraviolet light in a state in which the ultraviolet irradiation section 202 is extracted from the shared reagent storage container 110.

In a state in which the ultraviolet irradiation section 202 is inserted into the shared reagent storage container 110 and disposed within the shared reagent storage container 110, the second electric power switch 208 turns into the closed state.

The user of the analyzer 100 turns the reagent storage door 210 into the open state and feeds the reagent from the shared reagent storage container 110 to outside of this shared reagent storage container 110 for analysis. As a result, the shared reagent storage container 110 becomes empty. Owing to this, when the reagent suction nozzle 203 is extracted from the shared reagent storage container 110 for replacement of the shared reagent storage container 110 by a reagent storage container filled with the reagent, a state becomes the state shown in FIG. 4.

In the state shown in FIG. 4, when the first electric power switch 207 fails and the ultraviolet LED 204 continues to emit ultraviolet light, there is a concern that a person who replaces the shared reagent storage container 110 is exposed to the ultraviolet light.

The second electric power switch 208 functions to remove this concern. That is, even if the first electric power switch 207 fails, the second electric power switch 208 turns into the open state, intercepts the supply of the electric power to the ultraviolet LED 204, and can secure operator's safety at a time of extracting the reagent suction nozzle 203 from the shared reagent storage container 110.

In addition, it is possible to dispense with the position sensor provided in the elevating means disclosed in JP-1997-099921-A. Dispensing with the position sensor produces effects that the configuration is simple and inexpensive and reduction of a failure frequency can be expected.

The third electric power switch 209 will next be described.

The third electric power switch 209 supplies the electric power to the ultraviolet LED 204 and intercepts the electric power in accordance with a liquid amount of the reagent within the shared reagent storage container 110. That is, when a state of the liquid amount is such that the ultraviolet LED (ultraviolet generation section) 204 installed near the bottom surface of the shared reagent storage container 110 is located below a liquid level, to be irradiated with the ultraviolet light, of the reagent within the shared reagent storage container 110, the third electric power switch 209 supplies the electric power to the ultraviolet LED 204.

On the other hand, when the state of the liquid amount is such that the ultraviolet LED 204 is located above the lowered liquid level of the reagent as a result of feeding the reagent to outside of the shared reagent storage container 110 for analysis, the third electric power switch 209 intercepts the electric power to be supplied to the ultraviolet LED 204. This is intended to effectively execute irradiating the reagent, which is an object to be irradiated with ultraviolet light, within the shared reagent storage container 110 with the ultraviolet light.

Figure 5:
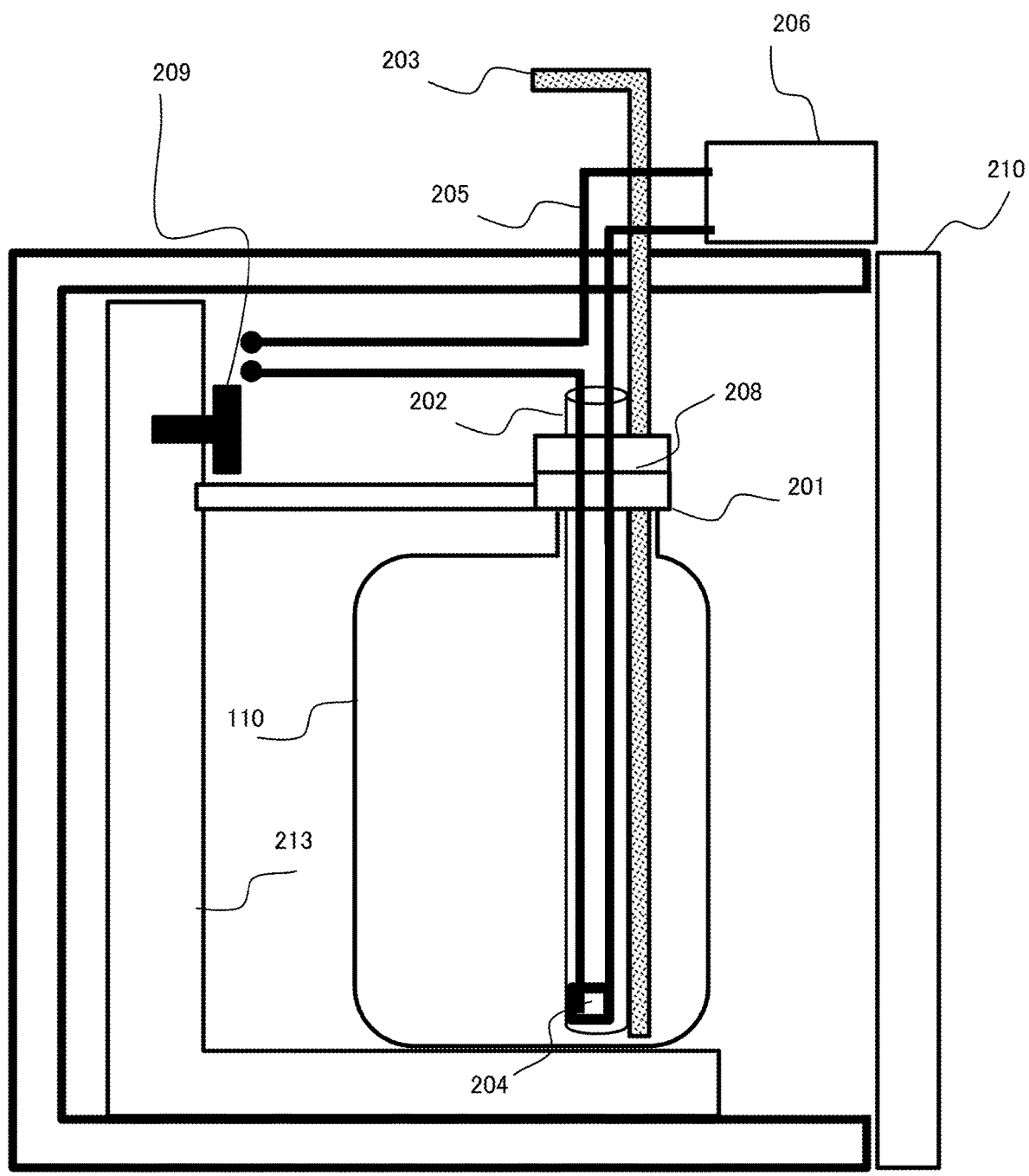
FIG. 5 shows a state in which an amount of the reagent within the shared reagent storage container is reduced and an ultraviolet LED is located upward of a liquid level of the reagent.

The third electric power switch 209 will be described with reference to FIG. 5. FIG. 5 shows a state in which the amount of the reagent within the shared reagent storage container 110 is reduced and the ultraviolet LED 204 is located upward of the liquid level of the reagent.

A weight switch is an appropriate example of the mounted electric power switch 209. The weight switch is incorporated into the holding stand 213 of the shared reagent storage container 110, and supplies the electric power to the ultraviolet LED 204 when a weight of the reagent exceeds a specified weight. While FIG. 5 shows a state in which the third electric power switch 209 is opened, FIG. 5 is a conceptual view of an open state of the electric power switch 209.

Reagents having an identical specific gravity have an identical volume relative to a weight. Therefore, reagents that are stored in the shared reagent storage containers 110 having an identical cross-sectional area and that have the identical specific gravity and the identical volume are identical in a height from the bottom surface of each shared reagent storage container 110. Using this fact, when the weight of the reagent stored in the shared reagent storage container 110 is heavier than the specified weight, then it is determined that the ultraviolet LED 204 is located below the liquid level within the shared reagent storage container 110, and the third electric power switch 209 turns into the closed state.

On the other hand, when the weight of the reagent stored in the shared reagent storage container 110 is lighter than the specified weight, then it is determined that the ultraviolet LED 204 is located above the liquid level within the shared reagent storage container 110, and the third electric power switch 209 turns into the open state.

Detection of the liquid level of the reagent stored in the shared reagent storage container 110 may be executed by a capacitance scheme using a capacitance of the residual reagent within the shared reagent storage container 110 or by a scheme of imaging a side surface of the shared reagent storage container 110 and detecting the liquid level.

As described so far, according to the first embodiment, the first electric power switch 207, the second electric power switch 208, and the third electric power switch 209 are connected in series between the ultraviolet LED 204 that emits ultraviolet light into the shared reagent storage container 110 for inhibiting the proliferation of microorganisms in the reagent within the shared reagent storage container 110, and the power supply 206 that supplies the electric power to this ultraviolet LED 204. The first electric power switch 207, the second electric power switch 208, and the third electric power switch 209 are simply configured with two contact points and a connection section that connects and disconnect these two contact points.

The first electric power switch 207 is opened when the reagent storage door 210 is opened, and the second electric power switch 208 is opened in response to an action of extracting the ultraviolet irradiation section 202 from the shared reagent storage container 110. In addition, the third electric power switch 209 is opened when the amount of the reagent within the shared reagent storage container 110 is equal to or smaller than the certain value. With this configuration, when any one of the first electric power switch 207, the second electric power switch 208, and the third electric power switch 209 is opened, the supply of the electric power to the ultraviolet LED 204 is intercepted.

Furthermore, the ultraviolet LED 204 is disposed in the shared reagent storage container 110 in such a manner that the irradiation direction of the ultraviolet LED 204 is the opposite direction to the direction toward the reagent storage door 210 approached by the operator.

Therefore, according to the first embodiment, it is possible to realize the analyzer that has the simple configuration, that is inexpensive, that can improve safety, and that can inhibit the proliferation of microorganisms using ultraviolet light.

Second Embodiment

A second embodiment will next be described.

The electric power switches 207, 208, and 209 in the first embodiment produce an effect of reducing the probability of exposure of the user of the analyzer 100 to the ultraviolet light in normal use of the analyzer 100; however, the electric power switches 207, 208, and 209 possibly complicate work for an operation check to the ultraviolet LED 204.

That is, in the first embodiment, it is necessary to simultaneously turn the first electric power switch 207, the second electric power switch 208, and the third electric power switch 209 into the closed state in the operation check to the ultraviolet LED 204. To satisfy the necessity, it is necessary that the reagent storage door 210 is in the closed state, the ultraviolet LED 204 is being inserted into the shared reagent storage container 110, and the liquid amount of the reagent is such that the ultraviolet LED 204 within the shared reagent storage container 110 is located below the liquid level of the reagent.

Loading a measurement system that can measure a dose of ultraviolet light even in a state of normally using the analyzer 100 into the analyzer 100 is a disadvantage from the viewpoint of a cost relative to a frequency of use.

Then, for the purpose of an operation check to the ultraviolet LED 204 in advance, an example of the second embodiment is configured such that, even when the first electric power switch 207, the second electric power switch 208, and the third electric power switch 209 are all in the open state, the electric power is supplied to the first ultraviolet irradiation section 202 by bypassing those switches, i.e., by making the connection in parallel to the first electric power switch 207, the second electric power switch 208, and the third electric power switch 209 and in series to the first ultraviolet irradiation section 202.

Figure 6:
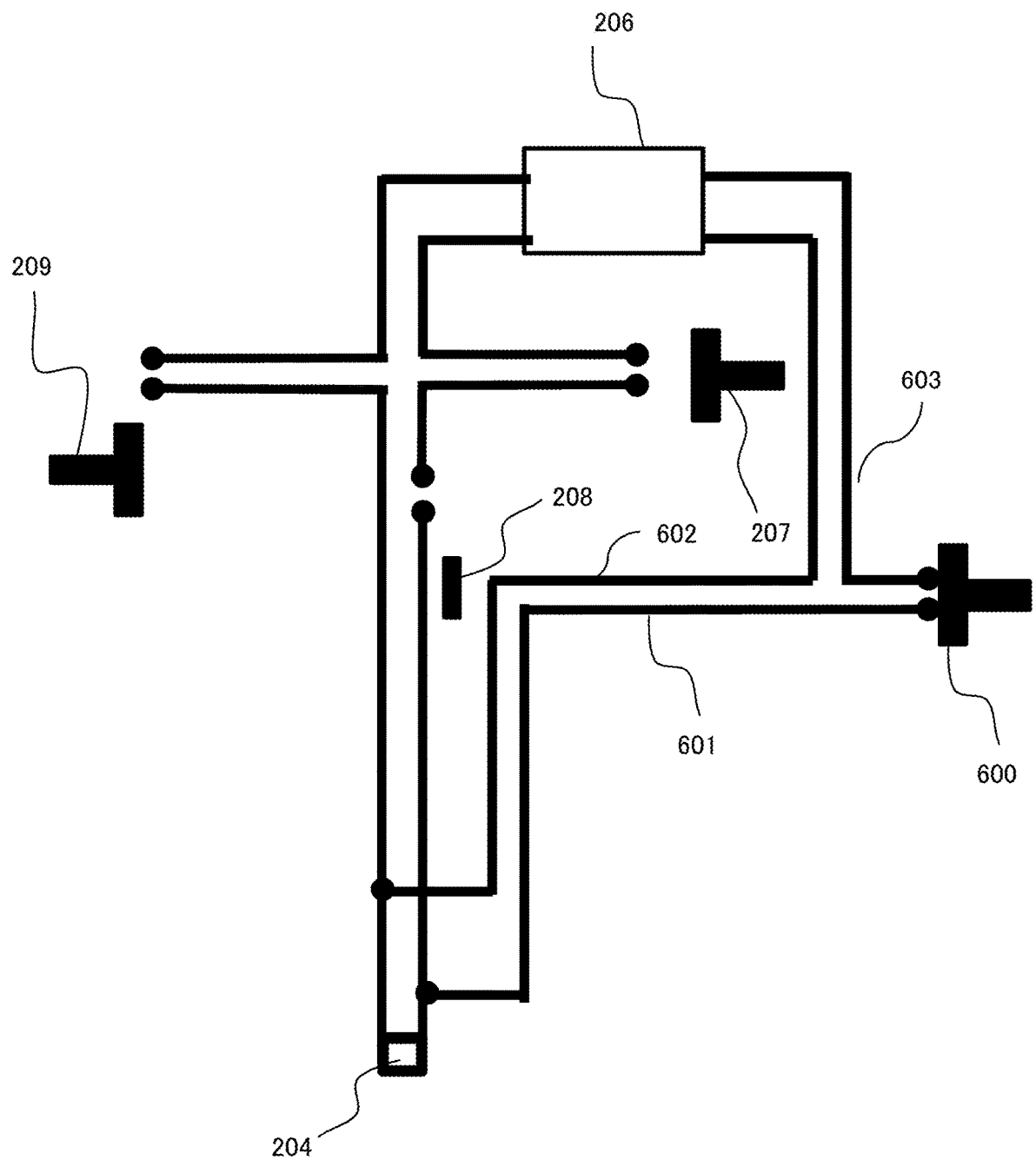
FIG. 6 is a schematic explanatory diagram of a second embodiment.

FIG. 6 is a schematic explanatory diagram of the second embodiment. Since a configuration of the analyzer 100 and configurations of the first electric power switch 207, the second electric power switch 208, and the third electric power switch 209 are similar to those in the first embodiment, detailed description of the configurations will be omitted.

FIG. 6 represents that the first electric power switch 207, the second electric power switch 208, and the third electric power switch 209 are all in the open state. Interconnection lines 601, 602, and 603 and a fourth electric power switch 600 are provided such that it is possible to execute the operation check to the ultraviolet LED 204 in this state. That is, the analyzer 100 is configured such that the interconnection lines 601, 602, and 603 and the fourth electric power switch 600 are connected to the power supply 206 and the ultraviolet LED 204 and that the electric power can be supplied from the power supply 206 to the ultraviolet LED 204 by closing the fourth electric power switch 600.

It is thereby possible to apply the electric power to the ultraviolet LED 204 by turning the fourth electric power switch 600 into a closed state even when the first to third electric power switches 207, 208, and 209 are opened.

If the reagent storage door 210 is in the open state while the fourth electric power switch 600 is in the closed state, an effect of shielding the ultraviolet light by the shared reagent storage container 110 and the reagent storage door 210 cannot be obtained. There is a concern that a person responsible for the operation check to the ultraviolet LED 204 is continuously exposed to the ultraviolet light. This is because the ultraviolet light is out of a visible light range and it is difficult for the operator to recognize whether the ultraviolet light is emitted from the ultraviolet LED 204.

To address the concern, according to the second embodiment, a material that discolors by exposure to the ultraviolet light is applied to a reagent storage room inner wall 700 of the reagent storage room where the shared reagent storage container 110 is accommodated.

Figure 7:
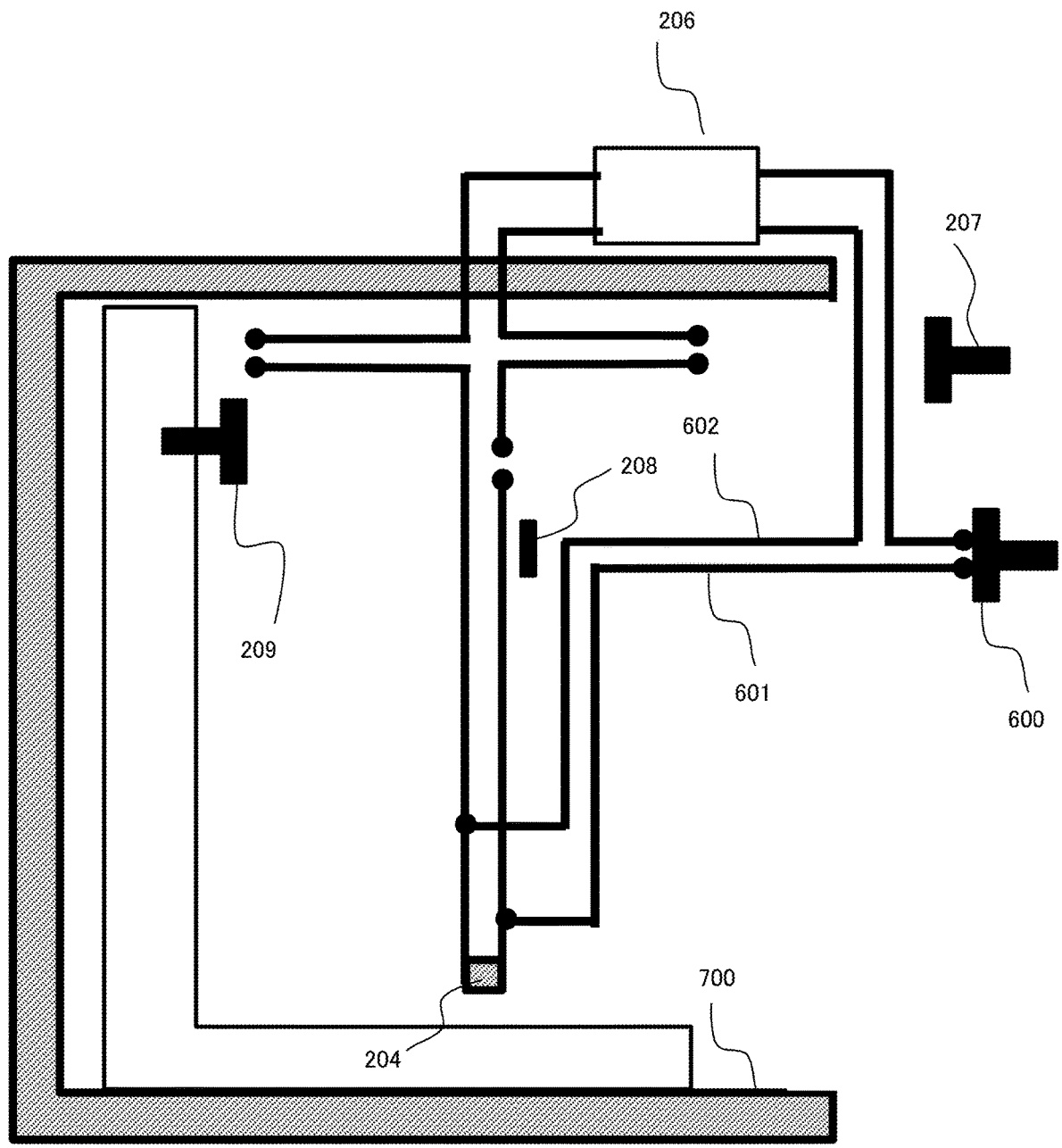
FIG. 7 is an explanatory diagram of a state in which a material that discolors by exposure to ultraviolet light is applied to a reagent storage room inner wall.

FIG. 7 is an explanatory diagram of a state in which the material that discolors by exposure to the ultraviolet light is applied to the reagent storage room inner wall 700. The sensitive material may be applied directly to the ultraviolet LED 204.

The fourth electric power switch 600 is installed in the analyzer housing exterior 211, the shared reagent storage container 110 is moved to an exterior of the reagent storage door 210, the reagent storage door 210 is opened, the first to third electric power switches 207, 208, and 209 are opened, and the fourth electric power switch 600 is closed at a position at which the operator is not irradiated with the ultraviolet light by the ultraviolet LED 204. Subsequently, the fourth electric power switch 600 is opened and the supply of the electric power to the ultraviolet LED 204 is stopped. Even in this state, the person responsible for the operation check can check the irradiation from the ultraviolet LED 204 when the material that discolors by exposure to the ultraviolet light discolors.

It is, therefore, possible to avoid continuous exposure of the person responsible for the operation check to the ultraviolet light.

Furthermore, the analyzer 100 according to the second embodiment has a display section that indicates that irradiation of the analyzer housing interior 212 with the ultraviolet light is ongoing during execution of the irradiation with the ultraviolet light from the ultraviolet LED 204. Detection as to whether the irradiation with the ultraviolet light is ongoing can be performed by, for example, determining whether the electric power is delivered through the normal interconnection line 205, the interconnection line 601, 602, or 603.

Figure 8A:
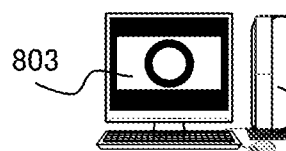
FIG. 8A shows an example in which a display section of a control section in the analyzer indicates whether irradiation with ultraviolet light is ongoing.
Figure 8B:
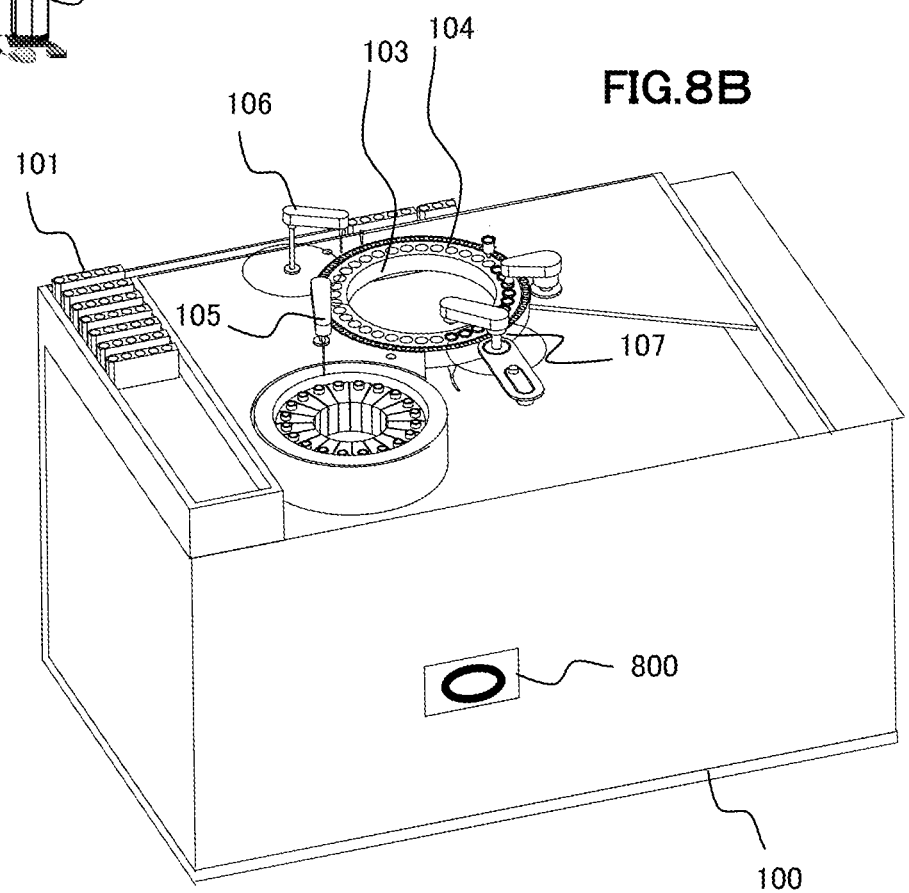
FIG. 8B is a schematic perspective view of an example in which a display section is provided on a side surface of a housing of the analyzer.

FIG. 8A shows an example in which a display section 803 of the control section 109 in the analyzer 100 indicates whether irradiation with the ultraviolet light is ongoing (and an example in which the display section is disposed in the control section 109 serving as the analysis section), and FIG. 8B is a schematic perspective view of an example in which a display section 800 is provided on a side surface of the housing of the analyzer 100. In addition, FIG. 8C shows an example of indicating whether the irradiation with the ultraviolet light is ongoing.

Figure 8C:
FIG. 8C shows an example of indicating whether the irradiation with ultraviolet light is ongoing.
Figure 8C:
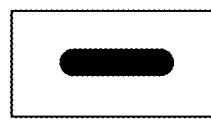

In the examples shown in FIGS. 8A and 8B, it is indicated in the display section 800 or 803 by a mark (circle) 801 shown in FIG. 8C that the irradiation with the ultraviolet light is ongoing and it is indicated by a mark (crossbar) 802 shown in FIG. 8C that the irradiation with the ultraviolet light is not ongoing.

As described above, indicating whether the irradiation with the ultraviolet light by the ultraviolet irradiation section 202 is ongoing enables the operator to easily check whether or not the ultraviolet light is ongoing.

The analyzer 100 may be configured such that any one of or each of the display section 803 of the control section 109 and the display section 800 on the side surface of the housing of the analyzer 100 indicates whether the irradiation with the ultraviolet light is ongoing.

If a main body of the analyzer 100 and the control section 109 are disposed at positions apart from each other, indicating whether the irradiation with the ultraviolet light is ongoing in the two display sections 803 and 800 can ensure that the operator checks the irradiation situation.

Alternatively, not signs such as the indications 801 and 802 shown in FIG. 8C but text representing content to the effect that the irradiation is ongoing or not ongoing may be indicated. In another alternative, the analyzer 100 may be configured such that an indication such as an indicator is lighted up or turned off.

The second embodiment produces not only similar effects to those of the first embodiment but also an effect that the operation check to the ultraviolet irradiation section 202 can be performed easily and safely.

While the embodiments described above relate to a case in which the present invention is applied to inhibiting the proliferation of microorganisms in the reagent within the shared reagent storage container 110, the present invention is also applicable to inhibiting the proliferation of microorganisms in a liquid (liquid used in the analyzer such as a diluent, a detergent, a buffer solution, or a surface-active agent) using the ultraviolet light. In the latter case, the analyzer is configured such that the liquid is irradiated with the ultraviolet light in a state of storing the liquid in a liquid storage container.

For example, the present invention is also applicable to inhibiting the proliferation of microorganisms in a reagent and system water within a pipe connected to a reagent dispensing probe of either the reaction reagent dispensing mechanism 105 or the shared reagent dispensing mechanism 107 on an interface between the system water and the reagent. In this case, a switch or the like are installed for turning on the ultraviolet LED 204 when an upper cover covering the analyzer 100 is closed and turning off the ultraviolet LED 204 when the upper cover is opened. It is noted that the pipe can be also defined as the liquid storage container.

Furthermore, while the analyzer 100 includes the first electric power switch 207, the second electric power switch 208, and the third electric power switch 209 in the first embodiment described above, the analyzer according to the present invention may include at least the first electric power switch 207 that is opened or closed in accordance with opening or closing of the reagent storage door 210.

An analyzer according to the present invention is configured to include: a liquid storage container (a reagent storage container 110, a pipe connected to a probe of a reaction reagent dispensing mechanism 105); an ultraviolet irradiation section 202; a power supply 206 that supplies electric power to the ultraviolet irradiation section 202; a liquid storage container storage room (a reagent storage room 220) that stores the liquid storage container and the ultraviolet irradiation section 202; a storage door (a reagent storage door 210, an upper cover covering the analyzer 100) that opens or closes the liquid storage container storage room 220 and that intercepts ultraviolet light; and a first electric power switch that supplies the electric power from the power supply 206 to the ultraviolet irradiation section 202 when the storage door is closed, and that stops supply of the electric power from the power supply 206 to the ultraviolet irradiation section 202 when the storage door is opened.

What is claimed is:

1. An analyzer comprising:
   an analysis section that analyzes a specimen within a reaction container that accommodates a reagent and the specimen;
   a liquid storage container that stores a liquid for use in analysis;
   an ultraviolet irradiation section that irradiates the liquid in the liquid storage container with ultraviolet light;
   a power supply that supplies electric power to the ultraviolet irradiation section;
   a liquid storage container storage room that stores the liquid storage container and the ultraviolet irradiation section;
   a first electric power switch that closes connection between the power supply and the ultraviolet irradiation section when a storage door of the liquid storage container storage room is closed, and that opens the connection between the power supply and the ultraviolet irradiation section and stops supply of the electric power to the ultraviolet irradiation section when the storage door is opened;
   a second electric power switch that closes the connection between the power supply and the ultraviolet irradiation section in a state in which the ultraviolet irradiation section is disposed in the liquid storage container, and that opens the connection between the power supply and the ultraviolet irradiation section and stops the supply of the electric power to the ultraviolet irradiation section in a state in which the ultraviolet irradiation section is extracted from the liquid storage container; and
   a third electric power switch that closes the connection between the power supply and the ultraviolet irradiation section in a state in which the ultraviolet irradiation section is disposed in the liquid storage container and in which an ultraviolet generation section of the ultraviolet irradiation section is located below a liquid level of the liquid stored in the liquid storage container, and that opens the connection between the power supply and the ultraviolet irradiation section and intercepts the electric power to be supplied from the power supply to the ultraviolet irradiation section in a state in which the ultraviolet irradiation section is disposed in the liquid storage container and in which the ultraviolet generation section of the ultraviolet irradiation section is located above the liquid level of the liquid stored in the liquid storage container;
   wherein
   the second electric power switch is connected in series to the first electric power switch,
   the third electric power switch is connected in series to the second electric power switch and the first electric power switch,
   and
   the third electric power switch is a weight switch that is opened or closed in response to a weight of the liquid stored in the liquid storage container.

2. The analyzer according to claim 1, further comprising a fourth electric power switch that is connected in parallel to the first electric power switch, the second electric power switch, and the third electric power switch, and that can supply the electric power to the ultraviolet irradiation section even when the first electric power switch, the second electric power switch, and the third electric power switch are all opened.

3. The analyzer according to claim 2, wherein a material that discolors by exposure to ultraviolet light is applied to an inner wall of the liquid storage container storage room.

4. The analyzer according to claim 2, further comprising a display section that indicates whether the ultraviolet irradiation section is generating ultraviolet light.

5. The analyzer according to claim 4, wherein
the display section is disposed on or in each of a side surface of a housing of the analyzer and the analysis section.

6. The analyzer according to claim 1, wherein
the liquid is the reagent and the liquid storage container is a reagent storage container.

7. The analyzer according to claim 6, wherein
an ultraviolet generation direction of the ultraviolet irradiation section is an opposite direction to a direction toward the storage door.

* * * * *